United States Patent [19]

Ludwig et al.

[11] Patent Number: 5,755,954
[45] Date of Patent: May 26, 1998

[54] METHOD OF MONITORING CONSTITUENTS IN ELECTROLESS PLATING BATHS

[75] Inventors: Frank A. Ludwig, Rancho Palos Verdes, Calif.; Cheryl Manger, East Greenwich; Kazimierz Wikiel, Wakefield, both of R.I.

[73] Assignee: Technic, Inc., Cranston, R.I.

[21] Appl. No.: 587,496

[22] Filed: Jan. 17, 1996

[51] Int. Cl.$^6$ .................................................. G01N 27/26
[52] U.S. Cl. .......................... 205/794; 427/304; 427/305; 427/306
[58] Field of Search ........................... 205/794; 427/304, 427/305, 306

[56] References Cited

U.S. PATENT DOCUMENTS

| | | | |
|---|---|---|---|
| 4,631,116 | 12/1986 | Ludwig | 204/434 |
| 5,320,724 | 6/1994 | Ludwig et al. | 204/153.1 |
| 5,324,400 | 6/1994 | Eliash et al. | 205/794 |
| 5,336,380 | 8/1994 | Phan et al. | 205/794 |
| 5,391,271 | 2/1995 | Ludwig | 205/794 |

*Primary Examiner*—Bruce F. Bell
*Attorney, Agent, or Firm*—Oppenheimer Poms Smith

[57] ABSTRACT

A method for monitoring the constituents present in an electroless plating bath solution. The method involves measuring ac spectra using a working electrode which has a high hydrogen overvoltage. First, a selected dc potential is applied to a working electrode which has been subjected to pretreatment and which is present in the electroless bath being analyzed. The electrode must have a high hydrogen overvoltage and is preferably an alloy of a low hydrogen overvoltage noble metal and a high overvoltage metal. A constant ac signal is superimposed on the dc potential. The dc potential is then swept over a chosen range at a selected sweep rate. The various constituents in the bath are then monitored by measuring the ac current at one or more reference phase angles with respect to the constant ac signal between the working electrode and a reference electrode as the dc potential is varied. The resulting ac spectra provides a useful measurement of the make-up of the constituents in the electroless plating solution. Regulation of solution temperature to optimize the ac spectra is also disclosed.

14 Claims, 4 Drawing Sheets

METHOD OF MONITORING CONSTITUENTS IN ELECTROLESS PLATING BATHS

BACKGROUND OF THE INVENTION

1. Field of the Invention

The present invention relates generally to plating baths and methods for monitoring the constituents contained therein. More particularly, the present invention relates to a voltammetric analysis method which is particularly suitable for rapid analysis of electroless plating baths. The method can be used to maintain desired concentrations of bath constituents to insure optimum plating bath performance.

2. Description of Related Art

The typical plating facility is composed of a multitude of baths for electrodeposition of numerous metals. Many of these baths involve electroplating of metals requiring means for applying electric current to the baths to carry out the electrodeposition of metals. However most plating shops also have tanks containing baths which, while also employing electrochemical processes for the electrodeposition of metals, do not require the application of electrical current to the bath. These deposition processes are referred to as "electroless plating". (Some types of conversion coating processes and all immersion plating processes also do not require the application of electric currents.) Electroless plating is based on the presence of a chemical reducing agent being added to the bath; these chemicals supply electrons to the substrate metal which transmits the electrons to the positively charged metal ions in the bath solution, reducing these ions to the metal in the same manner in which electric current reduces metal ions to metals in "nonelectroless", i.e. the common electrolytic or electrodeposition plating baths. The electroless plating of metals is of vast industrial importance and is used nearly as frequently in industry as electrolytic plating.

Electroless plating produces several unique results. Whereas it is difficult to obtain uniform deposit thickness of metal plate in crevices and holes with electrolytic plating, it is automatic and routine with electroless plating. This attribute is especially critical to the electronics industry, in which printed wiring boards must have uniform metal deposits plated into high aspect-ratio through-holes. Other properties and applications of electroless plating are deposits which can be produced directly upon nonconductors, deposits which are often less porous than electrolytic plating, and also deposits which often have unique chemical, mechanical or magnetic properties (such as higher hardness and wear resistance).

It is another characteristic of electroless plating that it occurs only on a catalytic surface; however the electroless plated deposit is always auto-catalytic, so that once the process has started it is self-perpetuating.

Electroless plating baths are otherwise similar to electrolytic plating baths. They both are comprised of a combination of several different electrochemical constituents. The specific constituents vary depending on the type of metal being plated, but in general can be broadly divided into what are commonly known as major constituents and trace, or minor constituents. The major constituents in electrolytic baths usually make up about 2 to 50% of the bath weight or volume, whereas in electroless baths the major constituents more likely are 0.1 to 2% of the bath weight or volume. Usually in electrolytic plating baths, soluble anodes are used of the same metal being plated so that the major metal concentration tends to remain fairly uniform. Also electrolytic baths do not have the requirement of a reducing agent as a major constituents since that function is provided by the external electric current. Therefore, because both the major constituents are there in low concentrations and they are not automatically replenished as in electrolytic processes, it is crucial to follow in real-time the concentration levels of the major constituents. If the major constituent levels drop too low, the rate of deposition becomes uneconomical; if the levels are too high, the catalytic selectivity for plating is lost, and the metal "drops out" throughout the bath proper rather than being restricted to the desired surface.

Current major constituent monitoring techniques typically involve removing a sample of the bath solution from the plating tank for subsequent wet or instrumental analysis. Typical methods of measuring major constituent concentrations of various types of plating baths are disclosed in K. E. Langford and J. E. Parker, "Analysis of Electroplating and Related Solutions", pages 83–100, 65–68 and 174–180. Wet or instrumental chemical analysis methods such as these usually must be performed by highly skilled personnel. Special and costly chemical analysis equipment and supplies are required. Furthermore, the delay between drawing the samples and receiving measurement results can be anywhere from several hours to several days.

Real-time methods for major constituents have been developed, but are not routinely used because of high cost and inconvenience in that often the solution must be pumped out of the plating tank into equipment of substantial size and complexity. Sometimes reagent solutions are automatically mixed with the pumped solution. Usually there is no room on a plating floor for close proximity of such equipment. Also the complexity of the automatic solution mixing and preparatory analytical steps result in low reliability and high cost. In addition, and perhaps of paramount importance, is that the methods and equipment are not universal in application, and therefore cannot be used for all the plating tanks in the plating shop. Methods included in these real-time, but low practicality procedures are ion-chromatography, differential pulse polarography, cyclic linear sweep voltammetric stripping, optrodes, and UV fluorescence.

The least impractical of these methods are probably the polarographic, voltammetric and optrode methods. The polarographic and voltammetric stripping methods are generally not suitable for electroless baths because the electroless process occurs at a "mixed potential"; the chemical reducing agent and the metal ion interact at one potential so that the electrochemical sensing signal from the stripping or polarographic electrode sensor will respond to both major constituents and cannot be deconvoluted into separate signals for each constituent. Also the cyclic voltammetric stripping technique gives only one response signal which is often as sensitive to trace constituents as major constituents and has been mainly used in plating baths to analyze for these trace constituents, and not major constituents.

The polarographic and stripping methods are not well suited to in-tank sensing, usually requiring solution pumping to the equipment. On the other hand optrode sensors have been placed into plating tanks, but their applicability has been limited to just a few optically active major constituents. They therefore totally lack universality in their application. UV fluorescence is also limited to a few active constituents, and is not suited to in-tank sensing.

A practical, inexpensive, real-time, in-tank method which has none of the above limitations is disclosed in U.S. Pat. No. 4,631,116, and is assigned to Hughes Aircraft Co., Los Angeles, Calif. However, the reproducibility, sensitivity and selectivity of the method is not as high in electroless baths as in electrolytic plating baths.

Accordingly, there is a present need to provide a real-time, in-tank method for monitoring major constituents in electroless plating baths and conversion coating baths. There is an additional need to provide a universal method and apparatus in which a single apparatus can be used to monitor bath chemistry of all the various electrolytic, electroless, immersion deposit and conversion coating baths which are present in many plating shops. Great advantages in terms of cost, scarcity of floor space, and equipment maintenance accrue if one apparatus located in a small room next to the shop floor can be multiplexed and connected by wires to individual sensors located in the individual plating and coating tanks on the shop floor. In this way a simple computerized apparatus could perform essentially real-time analysis for all shop tanks by a sequential multiplexing process.

SUMMARY OF THE INVENTION

In accordance with the present invention, methods are provided for monitoring constituents present in electroless plating baths. The present invention is based on the discovery that the monitoring methods disclosed in U.S. Pat. Nos. 4,631,116 and 5,320,724 may be modified, by choice of appropriate electrodes, to provide monitoring methods which are particularly well-suited for use in evaluating the constituents present in electroless plating baths.

The method of the present invention involves first applying a selected dc potential to a working electrode which has been subjected to annealing and anodic pretreatment and which is present in the electroless bath being analyzed. The electrode must have a high hydrogen overvoltage. A constant ac voltage is superimposed on the dc potential. The dc potential is then swept over a chosen range at a selected sweep rate. The various constituents in the bath are then monitored by measuring the ac current at one or more phase angles with respect to the constant ac voltage between the working electrode and a reference electrode as the dc potential is varied. The resulting ac spectra provides a useful measurement of the make-up of the constituents in the electroless plating solution.

As a feature of the present invention, it was also discovered that cooling the solution in the sensor while the ac spectra is being generated provides improvements in the ac spectra of the plating bath constituents. In particular, cooling an operating bath temperature from 90° C. to the order of 30° C. to 40° C. was found to provide preferred spectra.

The above discussed and many other features and attendant advantages of the present invention will become apparent as the invention becomes better understood by reference to the following detailed description when taken in conjunction with the accompanying drawings.

DETAILED DESCRIPTION OF THE INVENTION

As previously mentioned, a practical, inexpensive, real-time, in-tank method which has fair universality for most baths in a plating shop is disclosed in U.S. Pat. No. 4,631,116. The universality of this instrument has been augmented by succeeding patents, all assigned to Hughes Aircraft Co., Los Angeles, Calif., e.g. U.S. Pat. Nos. 5,252,192; 5,287,060; 5,296,124; 5,298,129; 5,296,123; 5,298,130; 5,298,131; 5,298,132; 5,298,145; 5,320,724. Although the above methods have been found to be well-suited for their intended purposes, there still has been a need for additional and continuing augmentation. As a result, we found that electroless plating bath analysis can be improved beyond the teaching found in U.S. Pat. No. 4,631,116. In that patent, a platinum working, i.e., sensing electrode, was used for all analyses. Gold working electrodes have also been used. The advantage of using very noble metals is that in many cases quite anodic potentials are used for pretreatment of the working electrode, as specified in U.S. Pat. No. 4,631,116. It has been found, however, that better analyses can be obtained for electroless baths by using materials for working electrodes which have high hydrogen overvoltages, rather than platinum which has a low hydrogen overvoltage. Such materials include, but are not limited to lead, tin, mercury and graphite.

The common electroless plating processes all employ reducing agents which evolve hydrogen gas in order to effectively fulfill their functions of reducing the metal ion to the metal. Exemplary electroless plating baths have the following constituents An electroless nickel bath contains: nickel chloride, sodium hypophosphite reducing agent, sodium citrate and sodium acetate A high deposition rate electroless nickel bath contains nickel chloride; sodium hypophosphite, lactic acid, propionic acid, and a trace amount of lead ion; a high rate electroless copper bath contains copper sulfate, sodium potassium tartrate, sodium hydroxide, sodium carbonate, Versente-T (EDTA+ triethanolamine), and formaldehyde reducing agent.

As a feature of the present invention, an electrode with a high hydrogen overvoltage is used. As a result, the electroless deposition process is blocked or, at least, hindered. Metals which are catalytic for electroless nickel are nickel, cobalt, steel, rhodium, palladium. These metals all exhibit fairly low hydrogen overvoltages at the deposition rates for electroless nickel. Noncatalytic metals, but which can be artificially induced to support electroless nickel deposition are copper, brass and silver. These metals have moderate hydrogen overvoltages. Artificial inducement is not possible on metals such as lead, cadmium, bismuth or tin. These metals exhibit high hydrogen overvoltages. Likewise, metals on which electroless copper can be successfully deposited are copper, gold, silver, iron, cobalt, nickel, platinum, palladium or rhodium, all fairly low in hydrogen overvoltage.

As the electroless process proceeds, diffusion gradients of metal ion and reducing agent are established at the surface of the substance being plated. Voltammetric procedures, such as those used in the present invention, are all dependent on the formation and change of these gradients as a function of applied voltage. In an electroless deposition, as explained previously, the plated surface is automatically held at a "mixed potential", established by the electroless deposition process itself. This mixed potential establishes a particular set of diffusion gradients. If a voltammetric procedure is now superimposed upon the plating process, a more complex set of diffusion gradients are established, which are not as amenable to simple analyses.

In accordance with the present invention, preferred analyses are obtained by using higher hydrogen overvoltage working electrodes, referred to as "hindered" or "non-catalytic" electrodes. Partially hindered electrodes are particularly preferred. These are defined as low or moderate hydrogen overvoltage noble metals or materials alloyed or mixed with high overvoltage metals or materials. Such partial hindering is induced by electrochemically treating platinum in a tin solution in order to produce a Pt-Sn alloy electrode. One procedure for producing such a Pt-Sn alloy electrode is taught in the literature as specified by E. Lamy-Pitara, et.al., *Journal of Electroanalytical Chemistry*, 372 (1994), p. 233–242. The advantage of the partial hindering produced by the Pt-Sn surface is that fundamental and second harmonic ac voltammetric procedures used in the present invention and in the prior referenced patents are especially suitable on non-catalytic and especially partially hindered electrodes because the electrode response of the non-diagnostic hydrogen evolution reaction is hindered, while at the same time the method does not prevent the electrolytic oxidation/reduction of the chemical reducing agent or of the plated metal ion. On highly catalytic platinum, the individual peaks for the reductant and oxidant are difficult to calibrate because of interferences between them and because of the complexity of the fine structure of the second harmonic peaks and valleys produced presumably by the hydrogen evolution reaction.

There also are other ways to reduce the catalytic activity of metals besides choosing high hydrogen overvoltage materials for the electrodes. Electroless nickel baths are operated between 85°–100° C. By cooling the bath solution to 30° C. by means of a bypass loop on the plating tanks, the catalytic properties of the Pt-Sn electrode are further decreased and an improved analysis of the bath is obtained. Accordingly, it is preferred that the solutions being monitored be cooled to temperatures on the order of 20°–40° C. during analysis.

Pure lead or tin electrodes dissolve under anodic pretreatment, which is often required in the methods of this invention, in order to retain the sensing electrodes in a reproducible, clean, and activated state. In these cases, mercury-wetted graphite, pure graphite, or such "partially hindered" electrodes as Pt-Sn, or other platinum or gold alloys are suitable. Other less common electrode materials such as boron or tungsten carbide, vitreous carbon or pyrolytic graphite are also suitable. An important aspect of this invention is that the choice of the correct amount of hindering for optimum analysis can either be chosen by the choice of the appropriate electrode materials or by a combination of appropriate electrode materials and choice of bath temperature within the sensors. The amount of hindering will usually be between about 30 and 90% of the hydrogen overvoltage on mercury. Hindering of electrodes is accomplished by electrodeposition and inclusion of non-catalytic material within the surface structure of noble metals materials, formation of appropriate alloys of low and high overvoltage metals by conventional thermal methods of preparing alloys, and choosing high hydrogen overvoltage materials as electrodes.

Another improvement of this invention is the use of a simple and convenient reference electrode made up of the same metal that is being plated. For example, in an electroless nickel bath, a nickel reference electrode is used, the area of which is appropriate to the internal volume of solution contained within the sensor. If the area to volume ratio is too low, a steady mixed potential reference voltage might not be established. If the ratio is too high the chemistry of the solution within the sensor may not be stable and/or the bath may "drop out" metal particles. It has been found that these reference electrodes provide steady potentials even if the temperature is significantly lower than the temperature required for acceptable plating rates. Changes in bath oxidant/reductant ratios have essentially no effect on the usefulness of these reference electrodes.

The present invention uses ac and dc voltammetric signals, generated using a common set of equipment, to provide accurate measurement spectra for mostly major, but also some trace constituents in a variety of electroless plating baths. In any given plating bath, certain voltammetric techniques may be more selective and sensitive than others for measuring a given constituent. Instead of applying separate techniques independently, the present method generates both ac and dc spectra for a plating bath. The method then uses the ac and dc spectra which provide the optimal spectral detail and therefore the best selectivity and sensitivity for the particular constituent concentrations. Some of the dc and ac methods involve interferences from other constituents. In order to maximize selectivity, those methods are chosen which minimize interferences. In some cases, minimization of interferences is provided by dc methods; but usually ac methods are found to be preferable.

Although the present description will focus on some exemplary voltammetric techniques, ac voltammetry as disclosed in U.S. Pat. No. 4,631,116 and specific dc voltammetry as disclosed in U.S. Pat. No. 5,320,724, it should be noted that the method of the present invention is not limited to these two techniques. The method can be used to combine any ac and dc voltammetric techniques to establish a flexible system for monitoring both major and trace constituents. Furthermore, although the following description applies the method to exemplary copper and nickel electroless plating baths, the present invention has wide application to many other electroless baths, and the constituents contained therein.

Figure 1:
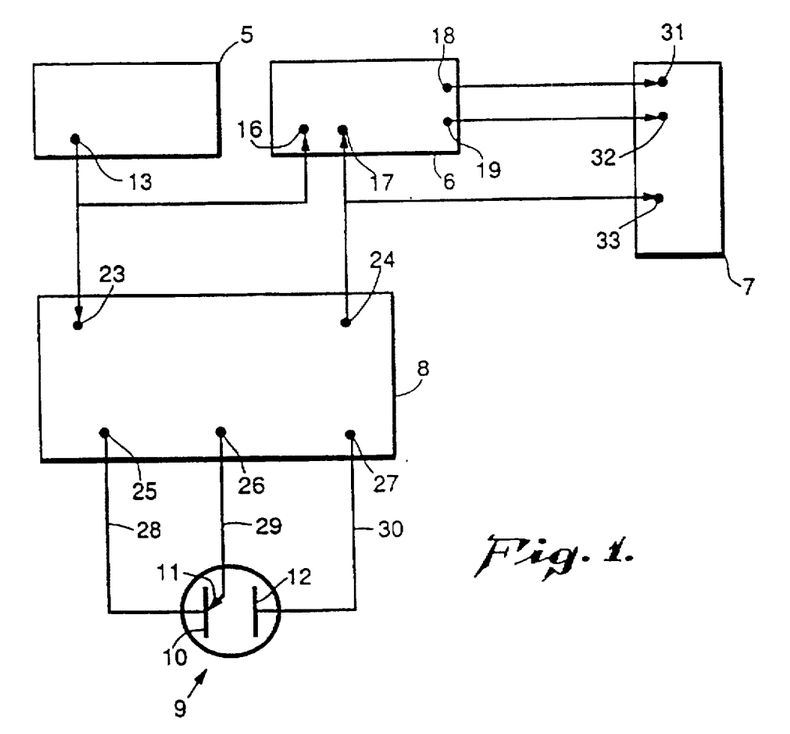
FIG. 1 is a schematic representation of a preferred exemplary system for conducting the method of the present invention.

The schematic diagram of FIG. 1 illustrates a preferred exemplary system for conducting the method of the present invention. This system is used to provide both ac and dc voltammetric signals, and is readily compatible with the equipment of U.S. Pat. No. 4,631,116 and U.S. Pat. No. 5,320,724. The contents of these patents are hereby expressly incorporated by reference. The present method thus extends the capability of the voltammetric techniques without requiring additional equipment.

In the exemplary system of FIG. 1, the plating bath solution is located within an electrochemical cell 9. The electrochemical cell 9 is preferably part of an in-tank electrochemical sensor submerged within the plating bath. The solution can be drawn through the in-tank sensor by a pump. The potentiostat 8 serves to generate electrode pretreatment signals of appropriate amplitude and duration. The pretreatment signal removes any absorbed organics or other contaminants from the working electrode 10 which might interfere with ac or dc voltammetric measurements. Alternatively, the pretreatment signal could be supplied by the function or waveform generator 5. Waveform generator 5 provides an output 13 which is a voltammetric signal of appropriate frequency and amplitude. The voltammetric signal is applied to the external input 23 of potentiostat 8 and as a coherent reference to the reference input 16 of a lock-in amplifier 6.

In the case of the ac voltammetric signal, the waveform generator 5 provides a constant amplitude ac signal to the external potentiostat input 23. This constant amplitude ac signal is superimposed on a sweep signal generated within potentiostat 8. Alternatively, the sweep signal could be supplied by a second external waveform generator (not shown). In some cases the voltammetric signal is simply the one generated within potentiostat 8, upon which the ac is superimposed. For ac and dc voltammetric signals, the potentiostat 8 further serves to insure that the voltammetric signal amplitude does not vary as a result of variations in current flow through the electrochemical cell 9.

The voltammetric signal output from potentiostat port 25 is then applied to the working electrode 10, a platinum wire (which is a "hindered" platinum wire as previously discussed), in the electrochemical cell 9 via line 28. The electrochemical cell 9 also contains a counter electrode 12 and a standard calomel or an appropriately sized mixed-potential reference electrode 11 as previously discussed. The reference electrode 11 and counter electrode 12 are connected to potentiostat ports 26, 27 via lines 29, 30, respectively. The electrochemical cell 9 with electrodes 10, 11 and 12 is a sensor design typically used in conjunction with voltammetric techniques. Other sensor designs could also be used. When either the ac or dc voltammetric signal is applied to the working electrode 10, a response current is generated between the working electrode 10 and the counter electrode 12. The response current signal parameters vary depending upon the electrochemical processes occurring at the surface of the working electrode 10. The electrochemical processes are a function of the constituent concentrations, and the response current is therefore responsive to these concentrations.

Both the superposed ac and dc voltammetric signal response currents are passed back through the potentiostat 8. From the potentiostat output 24 the response current is applied to the signal input 17 of lock-in amplifier 6 and to the external sweep input 33 of strip chart recorder 7 or to computerized data acquisition system 7. In the case of the ac voltammetric signal response current, the lock-in amplifier serves to separate out the desired ac response current and resolve the first or second harmonic into in-phase and quadrature components. The dc voltammetric signal, however, need not be resolved into components before being displayed or computer analyzed. Certain filters are used with system 7 to filter out the ac in certain instances.

The dc or ac response current harmonic which provides the best spectral resolution is the one which should be selected for measurement. The in-phase component of the ac response current is then passed from in-phase output 18 of lock-in amplifier 6 to a display signal input 31 of system 7. Similarly, the quadrature component is passed from quadrature output 19 of lock-in amplifier 6 to a second display signal input 32 of system 7. The system 7 displays the in-phase and the quadrature components of the ac response current as a function of the dc sweep voltage. Since the dc sweep rate for a specific constituent is usually constant, the voltage axis also can be represented as a time axis. This display represents a unique ac response current spectra which is indicative of constituent concentration levels within the solution.

The dc response current is also displayed by system 7. Alternatively, a separate display means could be used for the dc response current signals. The separate display could be a strip-chart recorder, a computerized digital data acquisition system, an oscilloscope or other suitable display means.

The specific equipment used in the exemplary system of FIG. 1, includes a Wavetek Model 188 waveform generator, a PAR 273 potentiostat and PAR 5210 lock-in amplifier. The Wavetek waveform generator is available from Wavetek San Diego, Inc. of San Diego, Calif. and the PAR equipment is available form Princeton Applied Research, Princeton, N.J.

In order to optimize the accuracy of the ac and dc response current spectra produced in accordance with ac and dc voltammetric techniques described above, it is necessary to vary a number of independent physical test parameters. For the ac voltammetric signals, these parameters include: 1) pretreatment signal amplitude and duration; 2) type of ac wave form (i.e., sinusoidal, square, triangular, etc); 3) ac signal peak to peak amplitude and frequency; 4) dc sweep signal voltage range and sweep rate; 5) ac response current harmonic measured (i.e., first (or fundamental), second, etc.); and 6) ac response current reference phase angle setting.

In some cases a constituent is determined by a dc voltammetric signal which is simply dc current resulting from the dc voltage sweep signal upon which the ac signal is superimposed.

In general, the dc parameters which should be varied to optimize the spectral detail for either the dc or ac response currents include: 1) pretreatment signal amplitude and duration; 2) type of dc plating signal wave form; 3) plating signal amplitude and duration; 4) type of stripping signal waveform; 5) stripping signal amplitude and duration; and 6) signal response current characteristic measured.

The above ac and dc voltammetric system parameters were independently varied to determine the preferred system parameters for monitoring constituents in accordance with the present invention. It should be emphasized that the parameter range limits described below are average and that the present invention may produce useful results with parameter values outside the specified ranges. In applying other voltammetric techniques in accordance with the method of the present invention, a similar set of parameters applicable to these techniques would have to be optimized.

All voltages are given with respect to a saturated calomel electrode. The dc or ac response current is culled from the combined waveform. Therefore, the ranges given below apply to both the dc and ac methods. In terms of both the dc and ac voltammetric signals, the working electrode, the "hindered" platinum wire for electroless copper is preferably pretreated using a dc signal with an amplitude of about −0.15 V for a duration of about 20 seconds. For electroless nickel the electrode was pretreated at +1.5 V for 5 seconds. A sinusoidal ac waveform with an amplitude value set between 10 to 100 mv root mean square (rms) and a frequency set between about 30 to 20,000 Hz is superimposed on a dc sweep signal which is swept over an amplitude with a maximum range of about +2.0 V to −2.5 V and reversed to voltages short of or up to about +2.0 V at rates set between about 10 and 1,000 mv/sec. This sweep signal encompasses both stripping and plating electrode voltages. Optimal spectral peak resolution is obtained using the first or second harmonic of the ac response current, measured using a phase angle offset ranging between approximately 0 and 90 degrees. Numerous variations, including holds for brief periods at certain dc voltages, dc steps rather than sweeps to certain voltages, and several rather than just one sweep reversal may also be used.

Frequently, a major constituent may produce a major perturbation of the dc response current over a significant range of dc potential. However, in electroless baths it has been found that dc peaks usually involve significant interference from other constituents and it is best to use the fundamental or second harmonic ac signals for analysis of the major constituents. A solution flow rate of zero to about 500 ml/min past the sensing electrode wire is also an important variable for both ac and dc methods.

Each type of plating bath is unique and has a unique set of conditions for obtaining optimum analysis, with the minimum interferences from other constituents.

An example of the optimization of the exemplary ac and dc voltammetric system of FIG. 1 to detection of specific plating bath constituents is as follows.

The method of the present invention was applied to the Technic, Inc. EN 9120 electroless nickel bath, available from Technic, Inc. of Cranston, R.I. This bath is maintained by analyzing for the major bath reagents, nickel and hypophosphite. Additions to the bath are made per Technic, Inc. instructions based on these two analyses. The procedure for these analyses involves the second harmonic in-phase spectra, but with the reference phase angle set at 45°. The ac signal is set at 1000 Hz and an amplitude of 25 millivolts rms. The electrode is pretreated at +1.5 V for 5 sec. The dc scan with the superposed ac signal is then started at +0.2 V, swept to −1.2 V and then reversed and swept back to +1.5 V at 100 mv/sec. The sweeps are then continued for 3 cycles from +1.5 V tp −1.2 V and back again to +1.5 V. Data is reproducible after 3 scans and can be taken on the fourth or following scans. The Pt-Sn wire electrode was produced by methods similar to those described in the *Journal of Electroanalytical Chemistry* 372 (1994) p. 233–242. In addition the electroless plating solution was cooled to 30° C. The platinum wire electrode was 1 mm in diameter and approximately ½ inch in length. A preliminary annealing pretreatment of the electrode has been found to be of importance. The wire is annealed in an oxidizing flame or gas furnace at temperatures just below the melting point of platinum for about 15 seconds prior to the hindering procedure described in the referenced article. It has been found that the annealing procedure is useful for all platinum sensing wires for electroless, electrolytic, immersion and conversion coating baths using the exemplary ac and dc voltammetric system and methods described earlier. Sensors annealed in this fashion give greater reproducibility. The measurements were obtained with bath solution flowing past the sensing electrode.

The nominal concentration of nickel in the bath was the recommended plating concentration of 0.75 oz/gal. The nominal hypophosphite concentration was 3.8 oz/gal. The data is presented in FIGS. 2, 3 and 4. The nickel peak is designated as N in the Figures and the hypophosphite peak as H. As can be ascertained from the figures the results shown in Table I were obtained.

TABLE I

Figure 2:
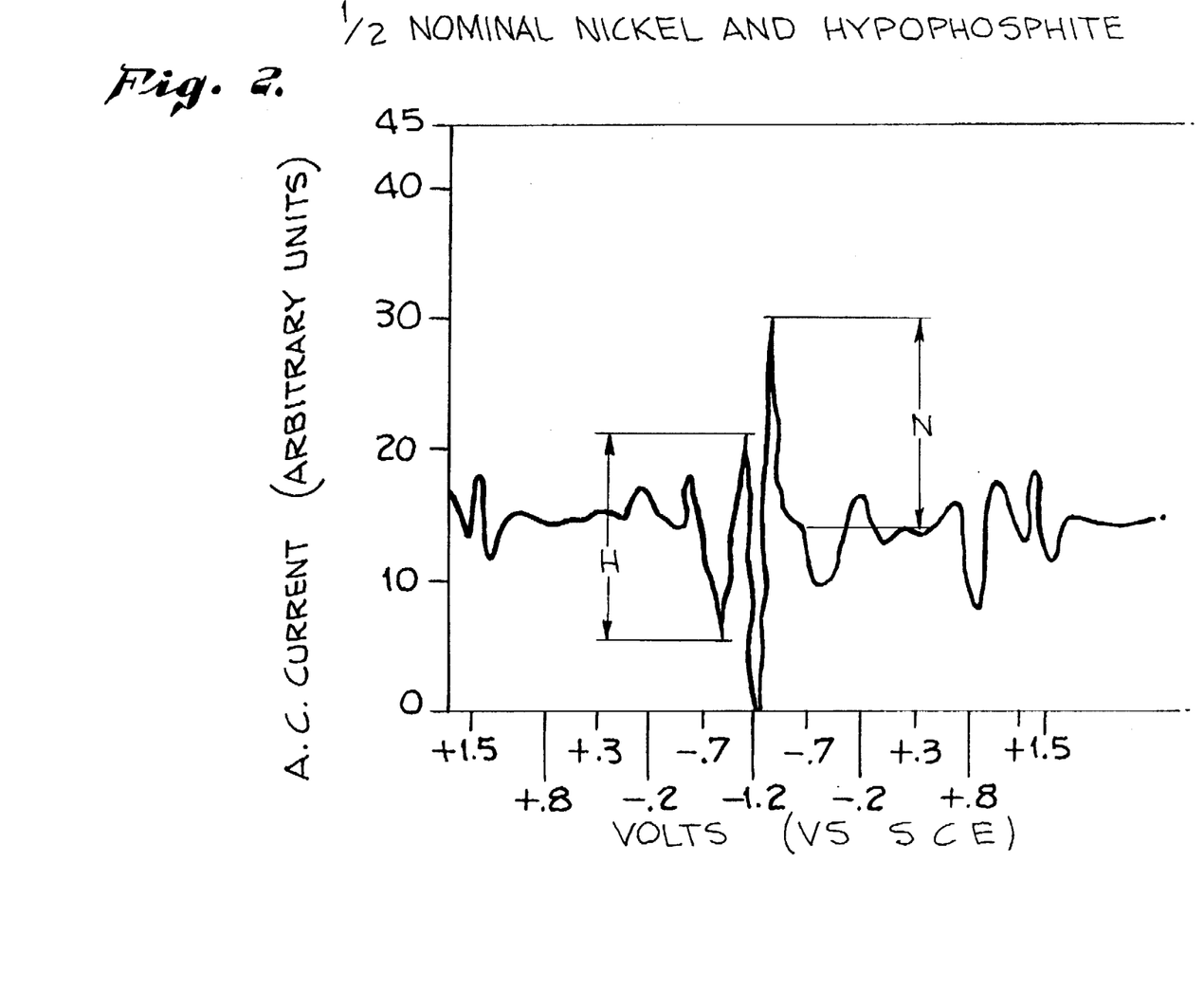
FIG. 2 displays in-phase second harmonic spectra for an electroless nickel bath at concentrations of ½ nominal of nickel and hypophosphite. The nickel measurement and peak is labeled N and the hypophosphite measurement and peak is labeled H.
Figure 3:
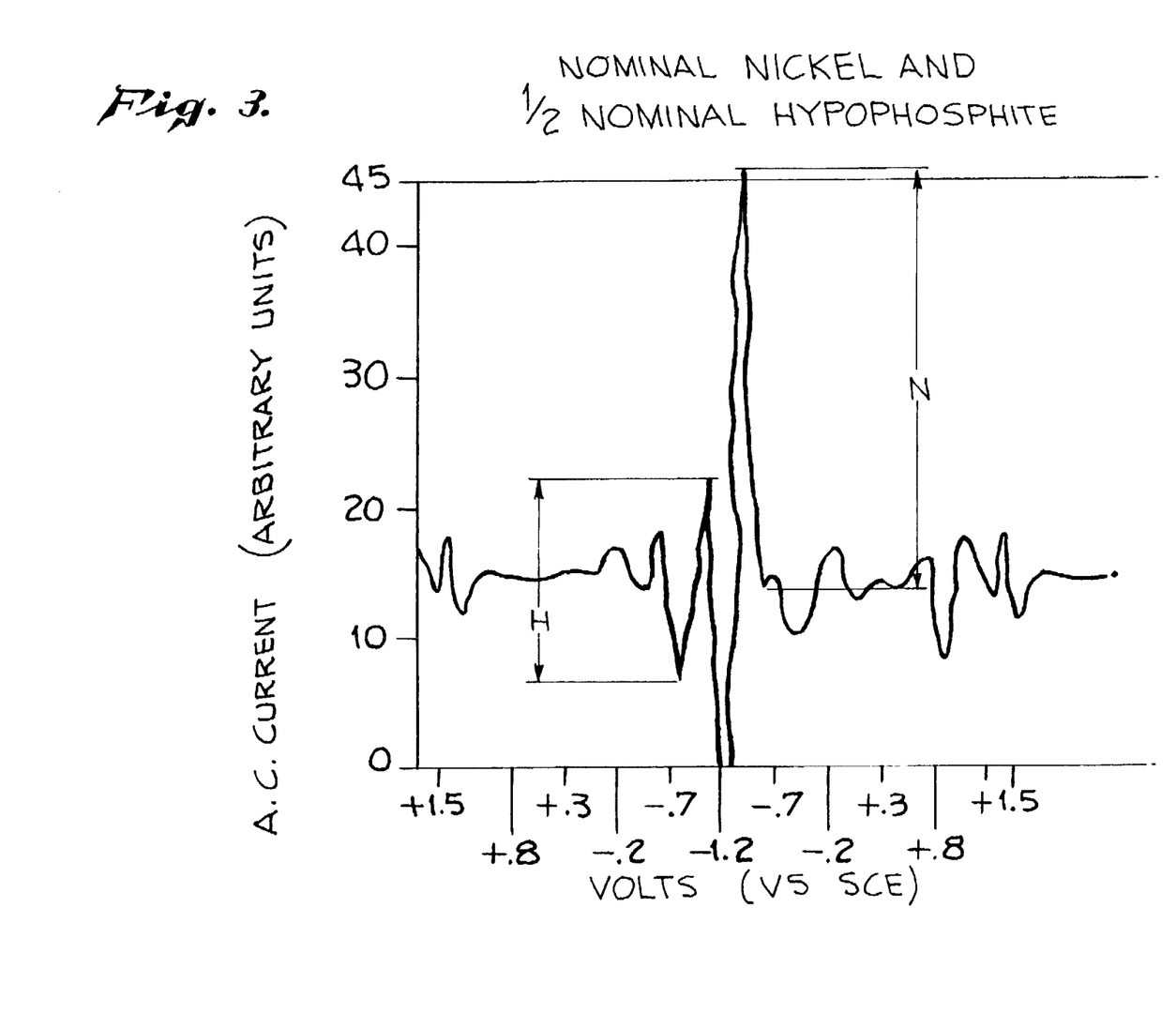
FIG. 3 displays the same spectra but under conditions of increased concentration to nominal nickel while retaining hypophosphite at ½ nominal.
Figure 4:
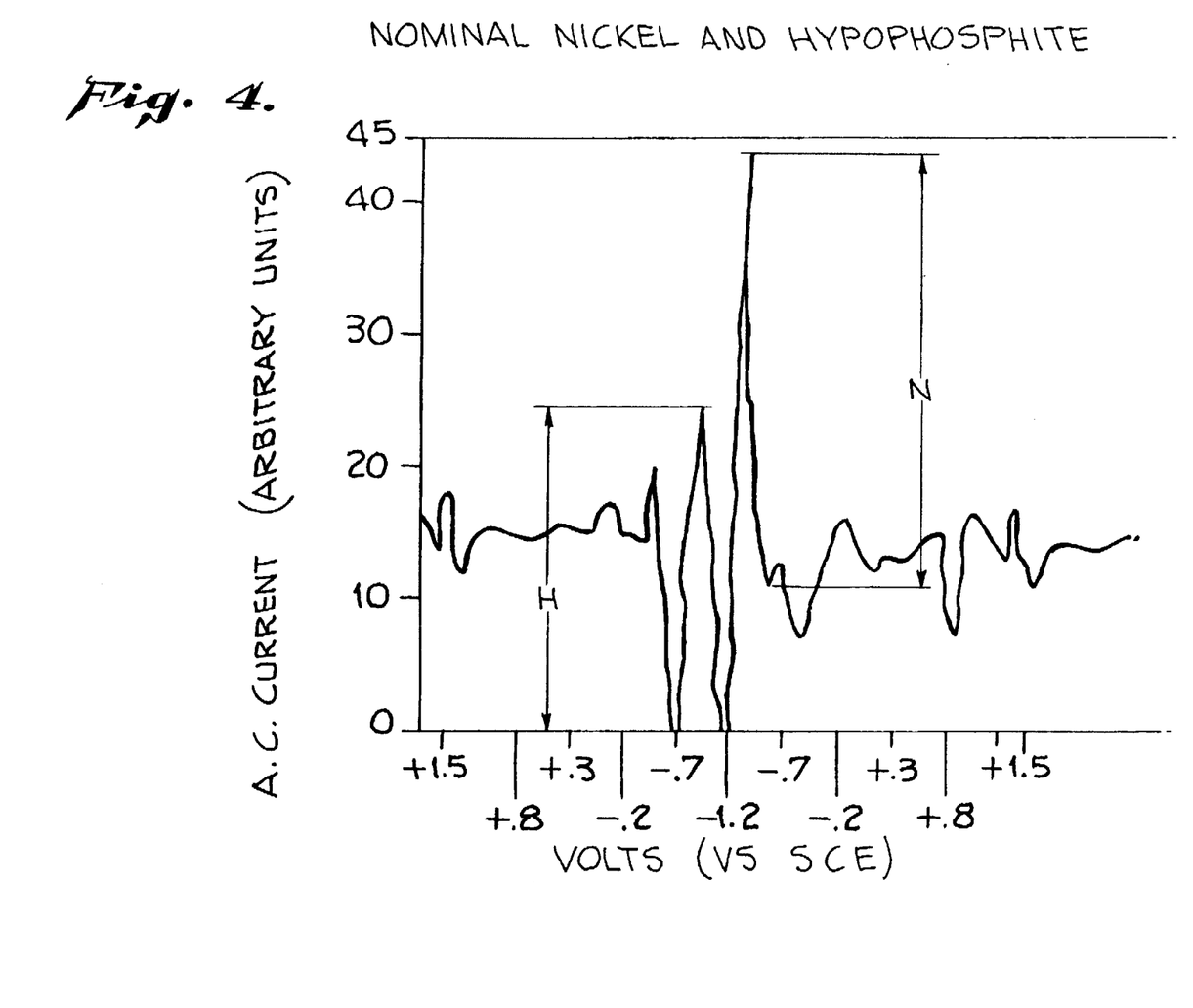
FIG. 4 displays the same spectra except that both concentrations have been increased to nominal.

| Bath Composition | ac current (arbitrary units) | |
|---|---|---|
|  | Ni | hypo |
| ½ nominal Ni and hypo | 16.0 | 15.2 |
| nominal Ni, ½ nom. hypo | 32.0 | 15.1 |
| nominal Ni and hypo | 32.5 | 24.8 |

The data indicates that doubling the nickel concentration does not interfere with the hypo determination and doubling the hypo concentration has very little effect on the nickel determination. A gold wire, a pure platinum wire, and a 3/16 inch diameter vitreous carbon disc sensing electrode were also used. The same system parameters were used. The carbon disc gave nearly identical results to those shown in Table I. However, the electrical pretreatment procedures were not effective in obtaining good reproducibility on the vitreous carbon electrode. Mechanical polishing was required, but even that did not accomplish the high degree of reproducibility obtained by electrical pretreatment and multiple scans on the Pt-Sn electrode. The gold and pure platinum gave essentially the same results, which were spectra with too much fine structure. The platinum and gold spectra could not be readily correlated to the Nickel and hypophosphite concentrations.

Whereas problems were evident using the calomel electrode at higher bath temperatures, a very stable and reproducible reference electrode was obtained by using a nickel plated sheet reference electrode which was of a size recommended by Technic for bath loading of parts being plated by their process; namely a bath loading of 0.1–0.8 ft.²/gal. The solution inclosed by the sensor body (see U.S. Pat. No. 5,296,123) was used for the bath volume; and the prescribed bath loading range was used for determining the reference electrode area. The mixed potential of this electrode served as a good reference electrode regardless of the bath constituent concentrations. This type of reference electrode is considered an important feature of this invention.

The method of the present invention was also applied to the detection of the constituents recommended for analysis by Technic, Inc. for their EC 70 Techni electroless copper bath. This bath is maintained by analyzing for copper, formaldehyde and sodium hydroxide. The copper and sodium hydroxide spectra were obtained as fundamental "first" harmonic ac spectra at a frequency of 160 Hz and an ac amplitude of 10 mv rms. The spectra were obtained on the out-of-phase quadrature axis with the reference phase angle set at 0°. For the copper analysis only the pretreatment of the hindered electrode (identical to the electrode of the previous example) consisted of −0.15 V for 20 sec. The entire determination of the copper was taken with a quiescent solution inside the sensor body. The dc sweep with the superposed ac was taken from −0.15 V to −1.5 V and reversed back to +0.2 V at a sweep rate of 50 mv/sec. The nominal compositions were 2.5 g/l for copper, 12.0 g/l for sodium hydroxide, and 3.1 g/l for formaldehyde. The sensor was kept at the plating bath temperature of 30° C.

The results are given in Table II.

TABLE II

| Bath Composition | ac current (arbitrary units) |
|---|---|
| nominal copper | 136 |
| 110% copper | 161 |
| 120% | 194 |

For sodium hydroxide the ac criteria were identical to those for copper, the pretreatment was 20 seconds at −0.15 V and the solution was quiescent, but the sensing electrode was then held at −1.5 V for 20 sec and then swept from −1.5 V to +0.2 V at a sweep rate of 100 mv/sec. The results are shown in Table III.

TABLE III

| Bath Composition | ac current (arbitrary units) |
|---|---|
| nominal Cu, NaOH, formaldehyde | 36.7 |
| 125% NaOH, nom. Cu, formaldehyde | 52.9 |
| 125% NaOH and Cu, nom. formaldehyde | 50.3 |
| 125% NaOH, Cu, formaldehyde | 49.2 |

For the formaldehyde analysis, the ac frequency remained at 160 Hz, the reference phase angle at 0°, but the amplitude was changed to 25 mv rms. Also, the determination was second harmonic on the in-phase axis. The solution was flowing past the electrode. The pretreatment was −0.15 V for 20 seconds, then swept from −0.15 to −1.0 V and reversed to 0.0 V, at 20 mv/sec. The results are given in Table IV.

TABLE IV

| Bath Composition | ac current (arbitrary units) |
| --- | --- |
| nominal Cu, NaOH, formaldehyde | 7.8 |
| 125% Cu, nom. NaOH, formaldehyde | 7.0 |
| 125% formaldehyde and Cu, nom. NaOH | 10.4 |
| 125% NaOH, Cu, formaldehyde | 11.4 |

The interferences are greater for the electroless copper than for the electroless nickel.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the above preferred embodiments, but is only limited by the following claims.

What is claimed is:

1. A method for monitoring the concentrations of constituents present in a solution used in an electroless plating process wherein said constituents affect plating deposit properties, said method comprising the steps of:
   (a) applying a selected dc potential to a working electrode which has been subjected to annealing and anodic pretreatment and is positioned within said solution containing said constituents, said working electrode being a non-catalytic electrode which comprises a low or moderate hydrogen overvoltage material which is alloyed or mixed with a high overvoltage material;
   (b) superimposing a constant ac voltage on said dc potential applied to said working electrode, said ac voltage having a root mean square potential and a frequency and producing an ac current;
   (c) varying said dc potential at a chosen sweep rate over a chosen range; and
   (d) measure said dc and/or said ac current or a harmonic thereof at one or more reference phase angles with respect to said constant ac voltage between said working electrode and a reference electrode positioned within said solution as said dc potential is varied over said range, said measurement of dc and/or ac current in relation to varying dc potential being expressed as dc and/or ac current spectra which are used to determine and monitor said constituents in said solution.

2. A method for monitoring the concentrations of constituents present in a solution used in an electroless plating process according to claim 1 wherein said high overvoltage material is selected from the group consisting of lead, tin, mercury, mercury-wetted graphite, vitreous carbon, pyrolytic graphite, cadmium, bismuth, tungsten carbide, boron carbide.

3. A method for monitoring the concentrations of constituents present in a solution used in an electroless plating process according to claim 2 wherein said high overvoltage material is metal selected from the group consisting of tin, cadmium, lead, mercury and bismuth.

4. A method for monitoring the concentrations of constituents present in a solution used in an electroless plating process according to claim 1 wherein said low or moderate hydrogen overvoltage material is selected from the group consisting of noble metals.

5. A method for monitoring the concentrations of constituents present in a solution used in an electroless plating process according to claim 4 wherein said noble metal is selected from the group consisting of platinum, palladium, rhodium and gold.

6. A method for monitoring the concentration of constituents present in a solution used in an electroless plating process according to claim 4 in which said material is annealed in an oxidizing flame or gas furnace at temperatures just below the melting point of the material.

7. A method for monitoring the concentrations of constituents present in a solution used in an electroless plating process according to claim 1 wherein said electrode comprises an alloy or mixture of platinum and tin.

8. A method for monitoring the concentration of constituents present in a solution used in an electroless plating process according to claim 7 wherein said electrode comprises sufficient tin on the surface of said electrode to produce a hydrogen overvoltage which is about 30 to 90% of the hydrogen overvoltage of a mercury electrode.

9. A method for monitoring the concentrations of constituents present in a solution used in an electroless plating process according to claim 1 wherein said electroless plating bath is an electroless nickel plating bath or an electroless copper plating bath.

10. A method for monitoring the concentration of constituents present in a solution used in an electroless nickel plating process according to claim 9 wherein a reference electrode is used in applying said selected dc and ac potentials and wherein said reference electrode is a nickel or nickel-plated sheet reference electrode.

11. A method for monitoring the concentration of constituents present in a solution used in an electroless nickel plating process according to claim 10 wherein said reference electrode has an area of 0.1–0.8 ft$^2$/gallon of solution enclosed by the sensor body.

12. A method for monitoring the concentrations of constituents present in a solution used in an electroless plating process according to claim 1 where the percentage of high hydrogen overvoltage material on the electrode surface is sufficient to produce an electrode which has about 30 to 90% of the hydrogen overvoltage of a mercury electrode.

13. A method for monitoring the constituents present in a solution used in an electroless plating process according to claim 1 wherein the temperature of said solution being measured is between 20° C. and 40° C.

14. A method for monitoring the concentration of constituents present in a solution used in an electroless plating process according to claim 1 wherein said solution is maintained at an operating process temperature during said plating process and wherein the temperature of said solution being measured is cooled to between 10° C. and 80° C. below said operating process temperature.

* * * * *